United States Patent [19]
Schick

[11] Patent Number: 5,861,142
[45] Date of Patent: *Jan. 19, 1999

[54] METHOD FOR PROMOTING HAIR, NAIL, AND SKIN KERATINIZATION

[76] Inventor: Mary Pichler Schick, 2027 Old Forge Way, Marietta, Ga. 30068

[*] Notice: This patent issued on a continued prosecution application filed under 37 CFR 1.53(d), and is subject to the twenty year patent term provisions of 35 U.S.C. 154(a)(2).

[21] Appl. No.: 621,473
[22] Filed: Mar. 25, 1996
[51] Int. Cl.[6] .................................................. A61K 7/06
[52] U.S. Cl. ..................... 424/61; 424/701; 424/451; 424/464; 424/484; 424/489; 514/365; 514/395; 514/937; 514/944
[58] Field of Search ................................... 424/401, 701, 424/451, 464, 484, 489; 514/365, 395, 937, 944

[56] References Cited

U.S. PATENT DOCUMENTS

| | | | |
|---|---|---|---|
| 3,915,986 | 10/1975 | Gyurik et al. | 260/309.2 |
| 3,928,375 | 12/1975 | Düwel et al. | 260/309.8 |
| 3,954,791 | 5/1976 | Loewe et al. | 260/309.2 |
| 4,145,431 | 3/1979 | Haugwitz et al. | 424/273 B |
| 4,159,337 | 6/1979 | Rowlands | 424/273 B |
| 4,166,858 | 9/1979 | Rowlands | 424/273 B |
| 4,792,610 | 12/1988 | Lachhein et al. | 548/329 |
| 4,871,544 | 10/1989 | Eckenhoff | 424/438 |
| 4,925,669 | 5/1990 | Dyer et al. | 424/438 |
| 5,036,069 | 7/1991 | Andrews et al. | 514/249 |
| 5,169,846 | 12/1992 | Crooks | 514/229.8 |
| 5,340,804 | 8/1994 | Wickiser | 514/150 |
| 5,432,187 | 7/1995 | Gazzard | 514/388 |
| 5,434,163 | 7/1995 | Edlind et al. | 514/310 |

FOREIGN PATENT DOCUMENTS

| | | |
|---|---|---|
| 1 132 906 | 10/1982 | Canada . |
| 0 025 696 | 3/1981 | European Pat. Off. . |
| 0 090 368 | 10/1983 | European Pat. Off. . |
| 0 187 012 | 7/1986 | European Pat. Off. . |
| 0 224 249 | 6/1987 | European Pat. Off. . |
| 1 565 896 | 4/1980 | United Kingdom . |
| 2 252 730 | 8/1992 | United Kingdom . |
| 95/13065 | 5/1995 | WIPO . |
| 95/16447 | 6/1995 | WIPO . |

OTHER PUBLICATIONS

*Biochemistry Pharm.*, The interaction of benzimidazole carbamates with mamnalian microtobule protein vol. 28, p. 2680–2682.

Davidse and Flach, "Differential Binding of Methyl Benzimidazol–2–yl Carbamate to Fungal Tubulin as a Mechanism of Resistance to this Antimitotic Agent in Mutant Strains of *Aspergillus Nidulans*", *Journal of Cell Biology,* vol. 72, 1977, pp. 174–193.

Fisher, et. al., "Efficacy of fenbenzalole and piperazine against developing stages of toxocara and toxascaris in dogs", *The Veterinary Record,* vol. 132, No. 19, May 8, 1943, pp. 473–475.

(List continued on next page.)

*Primary Examiner*—Jyothsna Venkat
*Attorney, Agent, or Firm*—Jones & Askew, LLP

[57] ABSTRACT

A method for promoting keratinization of the hair, nails, and skin on the body of an animal or human in which a therapeutic amount of a benzimidazole sufficient to cause keratinization is administered either systemically or directly to the site on the body at which keratinization is desired. The method is useful for the treatment of a wide variety of hair loss disorders in humans such as alopecia, is useful for the treatment of hair loss disorders in animals, is useful for enhancing the strength and length of fingernails and toenails in humans, and is useful for enhancing the strength and length of claws, horns, hooves and antlers in animals. The method is also useful for the topical treatment of fungal infections, for skin replacement or grafting, and for wound healing.

5 Claims, 10 Drawing Sheets

OTHER PUBLICATIONS

Hammerschlag, et. al., "Benomyl and Methyl–2–benzimidazolecarbamate (MBC): Biomedical, Cytological and Chemical Aspects of Toxicity to *Ustilago maydis* and *Saccharomyces cerevisae*", *Pesticide Biochem. and Physiology*, vol. 3, pp. 42–54.

R.J. Horton, "Benzimidazoles in a Wormy World", *Parasitology Today*, vol. 6, No. 4, 1990 p. 106.

Townsend and Wise, "The Synthesis and Chemistry Anthelmintic Benzimidazoles", *Parasitology Today*, vol. 6, No. 4, 1990, pp. 107–111.

E. Lacey, "Mode of Action of Benzimidazoles", *Parasitology Today*, vol. 6, No. 4, 1990, pp. 112–124.

Jordan, et. al., "Endoparasitism in dogs: 21,583 cases (1981–1990)", IAVMA, vol. 203, No. 4, Aug. 1993, pp. 547–549.

G.C. Coles, "The Biochemical Mode of Action of some Modern Anthelmintics", *Pestic. Sci.* vol. 8, 1977, pp. 536–543.

D. Düwel, "Fenbendazole. II. Biological Properties and Activity", *Pestic. Sci.*, vol. 8, 1977, pp. 550–555.

H. Loewe, et. al. "Fenbendazole. I. Structure—Activity Relationships", *Pestic. Sci.*, vol. 8, 1977, pp. 544–549.

D.W. Gottschall, et. al., "The Metabolism of Benzimidazole Anthelmintics", *Parasitology Today*, vol. 6, No. 4, 1990, pp. 115–124.

Q.A. McKellar et. al., "The Benzimidazole Anthelmintic Agents—a review", *J. Pharmacol. Therap.* vol. 13, 1990, pp. 223–247.

M. Murray et. al., "Hepatic Microsomal Metabolism of the Anthelmintic Benzimidazole Fenbendazole: Enhanced Inhibition of Cytochrome P450 Reactions by Oxidized Metabolites of the Drug", *Chem. Res. Toxicol.* vol. 5, 1992, pp. 60–66.

J.P. Seiler, "The Mutagenicity of Benzimidazole and Benzimidazole Derivatives", *Mutation Research*, vol. 17, 1973, pp. 21–25.

J.P. Seiler, "Toxicology and Genetic Effects of Benzimidazole Compounds", *Mutation Research*, vol. 32 1975, pp. 151–167.

D.W. Woolley, "Some Biological Effects Produced by Benzimidazole and Their Reversal by Purines", (Laboratories of The Rockefeller Institute for Medical Research, New York) No. 17, 1943.

B.L. Blagburn et. al., National Prevalence of Canine Parasites based on Centrifugal Sucrose Flotation Examination of Fecal Specimens: Preliminary Report (18); *Proc. AAVP*, 1994, p. 57.

C.K. Fenger et. al., "The Phylogenetic Relationship of *Sarcocystic Neurona* to Other Coccidia Determined by Molecular Comparisons" (82), *Proc. AAVP*, 1994, p. 57.

S.C. Barr et. al. "Clinical Experience of Treating Cyrptosporidiosis in Cats and Dogs with Paromomycin", (79) *Proc. AAVP*, 1994, p. 56.

P.M. Schantz et. al., "Intestinal Parasites are Common in Pound Dogs in Fulton County, Georgia" (80); *Proc. AAVP*, 1994 p. 56.

B.T. Huss et al., "Fatal Cerebral Coenurosis in a Cat", (70), *Proc. AAVP*, 1994.

C.T. Faulkner et. al., "Gastrointestinal Parasitism in Dogs in Tennessee (1986–1992)" (71), *Proc. AAVP*, 1994.

METHOD FOR PROMOTING HAIR, NAIL, AND SKIN KERATINIZATION

The present method relates to the field of dermatology and more specifically relates to a method for promoting the keratinization of hair, nails, and skin of an animal or human.

BACKGROUND OF THE INVENTION

For centuries, humans have been preoccupied with the length, thickness, color, and quantity of hair. Hair thinning, receding hairlines, and hair loss can detrimentally affect appearance and self-image and can even result in significant emotional consequences.

Hair is a cylinder of keratinized cells protruding from a hair follicle that anchors the hair in the skin. All hair follicles in mammals have the same basic structure. Hair follicles in an adult human are generally arranged in groups of three. No new follicles are created or destroyed after birth, however, the type of hair produced by a given follicle can change. Most of the hairs on the scalp are terminal hairs, which are the coarse, pigmented, long hairs in which the bulb of the hair follicle is seated deep in the dermis. The short, fine hairs found on the scalp and elsewhere on the body are vellus hairs. Vellus hairs are non-pigmented and unmedullated, having the hair bulb located superficially in the dermis.

In humans, each hair follicle goes through repeated cyclical periods of growth including an active growth stage (anagen), which can persist for approximately 2 to 6 years; a transition phase (catagen), which lasts for only a week or two; and a resting period (telogen), which lasts 3 to 4 months. The hair is shed at the end of the telogen phase, and a new hair is grown as the cycle repeats. In the human scalp, which contains approximately 100,000 hair follicles, normally about 86% are in anagen, 1% are in catagen and 13% are in telogen. Therefore, in a normal human adult, approximately 100 hairs are shed from the scalp per day.

Excessive hair loss, or alopecia, may be classified as being one of two types, non-scarring alopecia and scarring alopecia, and can be caused by a wide variety of factors. For example, non-scarring alopecia has been attributed to genetics and advanced age; administration of drugs such as anti-cancer chemotherapeutic drugs and contraceptives; topical use of chemical treatments, such as hair dyes, permanent wave solutions, and straighteners; diseases, such as leprosy or syphilis; illness; allergy; and hair follicle infection. Scarring alopecia may be a consequence of burns (accidental or post surgical from cryosurgery or laser surgery) or trauma, which often causes follicle destruction. Therefore, humans and other animals exhibiting scarring alopecia may lack hair follicles in the region devoid of hair, whereas those with non-scarring alopecia possess hair follicles with short, fine, translucent hairs.

The most common type of human hair loss is androgenic alopecia (also known as androgenetic alopecia), which is a non-scarring hair loss of telogen hairs caused by an excessive androgen effect in genetically susceptible men and women. Androgens trigger the miniaturization or atrophy of terminal follicles that normally produce thick scalp hair and transforms them into vellus-like follicles, eventually yielding fine, downy hair that is barely perceptible. Androgenic alopecia is expressed in males as baldness of the vertex of the scalp and is commonly referred to as male pattern baldness. In females, androgenic alopecia appears as diffuse hair loss or thinning of the frontoparietal areas. As alopecia progresses with age, hairs in these predisposed areas miniaturize and appear to change from terminal hairs to resemble vellus hairs. In addition, as androgenic alopecia continues, the number of hairs in the active growth anagen phase decreases while there is an increase the number of hairs in the telogen phase.

Telogen effluvium is a type of non-scarring alopecia in which the anagen hairs prematurely move into the telogen phase. One most easily recognizable cause of telogen effluvium is the postpartum state in humans and other mammals. In the postpartum period, an increased number of hairs go into telogen due to the physical stress or hormonal changes associated with delivery. Three to four months later, there is considerable, but usually temporary hairloss. The hair usually returns to its normal state in six to twelve months. Other causes of telogen effluvium in humans and other mammals include physical stress and systemic illness, psychological stress caused by major life events such as a family death or divorce, medical nutritional deficiencies (kwashiorkor), or absolute calorie deprivation (marasmus, crash diets), vitamin and trace element deficiencies (zinc, biotin, essential fatty acids, and iron), and endocrine abnormalities (hypothyroidism, hyperadrenalcorticalism, hyperprolactinemia and adrenogenital syndrome).

Numerous remedies for hair loss have been attempted ranging from wigs, toupees, and other hairpieces to the oral or topical administration of hair growth solutions. No known cure has been discovered, even though many attempts have been made. Hair transplantation is one method of treatment that has shown some success. Single hairs or plugs of thick, growing hair are transplanted from one region of the scalp to the site of hair loss. This method is very expensive, time consuming and painful. Other hair growth stimulation methods, including ultra-violet radiation, scalp massage, revascularization surgery and acupuncture, have been tried with minimal or a total lack of success. The pharmaceutical drug minoxidil (2%, known commercially as Rogaine®, Upjohn Co., Kalamazoo, Mich.), originally discovered as a vasodilator for the treatment of severe hypertension, has been found to be somewhat useful as a hair growth stimulant in humans with androgenic alopecia. However, the drug has exhibited adverse effects. When taken orally, minoxidil has serious cardiovascular side effects such as fluid retention, tachycardia, and increased frequency of angina or new onset of angina, especially in persons with poor coronary circulation. Fluid retention can lead to weight gain, edema, heart failure and pleural or pericardial effusion. Although topical administration of minoxidil has fewer side effects, at least four months of continuous topical applications twice daily are required before partial reversal of follicular miniaturization may be observed, resulting in larger, more pigmented hairs and less hair shedding, giving the appearance of hair growth.

Hair or fur loss is also prevalent in wild and domesticated animals, especially mammals. Although animals are not psychologically impacted by their loss of fur or coat, their owners often are. In addition, fur loss in animals whose fur is sheared or otherwise used commercially may cause fur producers to suffer economically. Animal fur or hair loss has been attributed to many factors including disease, diet, metabolic disorders, insect bites, follicle infection, allergies, and hot spots or other hair or fur erosions caused by excessive biting, chewing and scratching. Currently, the only way to combat hair loss in animals is to attempt to remove the underlying disorder or restrain the animal to prevent access to the hair loss site. Oftentimes the disorder is successfully treated, but the fur is not completely restored.

Fingernails and toenails in humans and primates and their corresponding claws, hooves, horns and antlers in animals are composed of differently keratinizing cells. Human nails have lost most of their functional significance but remain important for cosmetic reasons. Animals use their claws, hooves, horns and antlers as weapons, tools and outward signs of dominance. Nail disorders range from premature breakage or roughness of the portion of the nail extending from the tip of the digit to total loss or destruction of the nail plate. For example, nail breakage caused by the splitting and resultant flaking of nails into layers horizontal to the longitudinal nail plate surface, referred to as onychoschizia, is caused by abnormal keratinization.

Nail disorders can also be caused by advanced age; infection from bacteria, fungi, yeast or mites (scabies); trauma; congenital or hereditary defects; hyperplasias such as warts, lesions, cysts and tumors; constant wetting of the hand or foot; psoriasis; disease states such as Darier's disease, *Lichen planus, Alopecia areata,* and twenty-nail dystrophy; contact irritation or allergy to chemicals such as those contained in nail polish, hardeners or adhesives; metabolic disorders, such as thyroid dysfunction; circulatory disorders; arthritis; *Periungual telangiectasia,* commonly observed in dermatomyositis patients and *lupus erythematosus* patients; and pharmaceutical or illicit drug use.

Skin is the ultimate barrier against infection. Patients suffering from burns or other trauma to the skin are at extreme risk for disease caused by microorganisms. Skin grafting procedures have been used in some circumstances, however, limited success has been achieved due to graft rejection or insufficient skin growth to cover the injured area. A method for promoting in vitro autologous, epidermal cell propagation or enhancing in vivo skin growth or wound healing would be extremely useful for replacing the skin barrier prior to the onset of life-threatening infection.

The disadvantages of the hair loss, nail claw, hoof, horn and antler disorders, and skin replacement treatments currently available are that they can be expensive, may cause adverse side-effects, and are not always effective for all patients. Therefore, there is an on-going need for development of new methods for treating hair or fur loss, nail, claw, hoof, horn or antler disorders, and skin replacement or wound healing in humans and animals.

SUMMARY OF THE INVENTION

A method for promoting keratinization on the body of an animal or human is described. In accordance with the method, a therapeutic amount of a benzimidazole composition sufficient to cause keratinization of the hair, nails or skin is administered. Administration may be either systemically or directly to the site on the body at which keratinization is desired.

The method is useful for the treatment of a wide variety of hair or fur loss disorders in humans and animals caused by a wide variety of diseases and disorders, particularly androgenic alopecia and telogen effluvium. In addition, the method is useful for normalizing keratinization in humans and animals with abnormal keratinization processes that manifest themselves visibly as fingernails, toenails, claws or hooves that are soft, easily bent and broken, frayed, split, or deformed in shape. The method is also useful for enhancing the strength and length of normal nails, for enhancing wound healing or skin grafting by promoting the propagation of epidermal cells, and to combat cutaneous fungal infections, particularly fungal infections of the nails and skin.

A benzimidazole is a compound containing a bicyclic ring structure in which benzene is fused to the 4- and 5-positions of an imidazole and includes benzimidazoles, benzimidazole carbamates and benzimidazole prodrugs. Benzimidazole prodrugs include phenylguanidines such as, but not limited to, fenbantel, netobimin and thiophanate. Preferred benzimidazole carbamates for use in the present method include, but are not limited to, thiabendazole, albendazole, flubendazole, mebendazole, ciclobendazole, parbendazole, oxibendazole, fenbendazole, and metabolites, such as fenbendazole sulfone, and derivatives thereof. The most preferred benzimidazoles are fenbendazole, fenbendazole prodrugs, and the sulfoxide metabolites of fenbendazole, such as oxfendazole (fenbendazole sulfoxide).

The benzimidazole compound is combined with an appropriate carrier or solvent to provide a benzimidazole composition. A preferred carrier is a pharmaceutically acceptable carrier. A most preferred carrier is a hair or nail cleansing, treatment, or cosmetic product such as shampoo or nail polish remover. The benzimidazole compound is prepared in granular, crystalline, powder, or amorphous form. The amorphous, stabilized benzimidazoles and their metabolites and derivatives are especially preferred because they are more highly soluble, bioavailable, and efficacious than crystalline benzimidazole. The benzimidazole composition is given systemically, preferably by oral administration, or is given locally by injection or topical application for parenteral absorption. The preferred method of administration is topical.

It is therefore an object of the present invention to provide a safe, inexpensive, and painless method for the treatment of hair loss.

It is a further object of the present invention to provide a method for the prevention or minimization of hair loss.

It is a further object of the present invention to provide a method for strengthening fingernails and toenails.

It is a further object of the present invention to provide a method for strengthening animal claws, horns, hooves and antlers, especially the hooves of horses, particularly race horses.

It is a further object of the present invention to provide a method for promoting normal hair and nail growth.

It is a further object of the present invention to provide a method for promoting skin growth and wound healing.

It is a further object of the present invention to provide a method for treating fungal infections of the skin and nails.

It is a further object of the present invention to provide a topical scalp treatment composition to minimize hair loss and a topical nail treatment composition to promote nail integrity.

These and other objects of the present invention will become apparent after reading the following detailed description of the disclosed embodiments and the appended claims.

DETAILED DESCRIPTION OF THE DISCLOSED EMBODIMENTS

Figure 1:
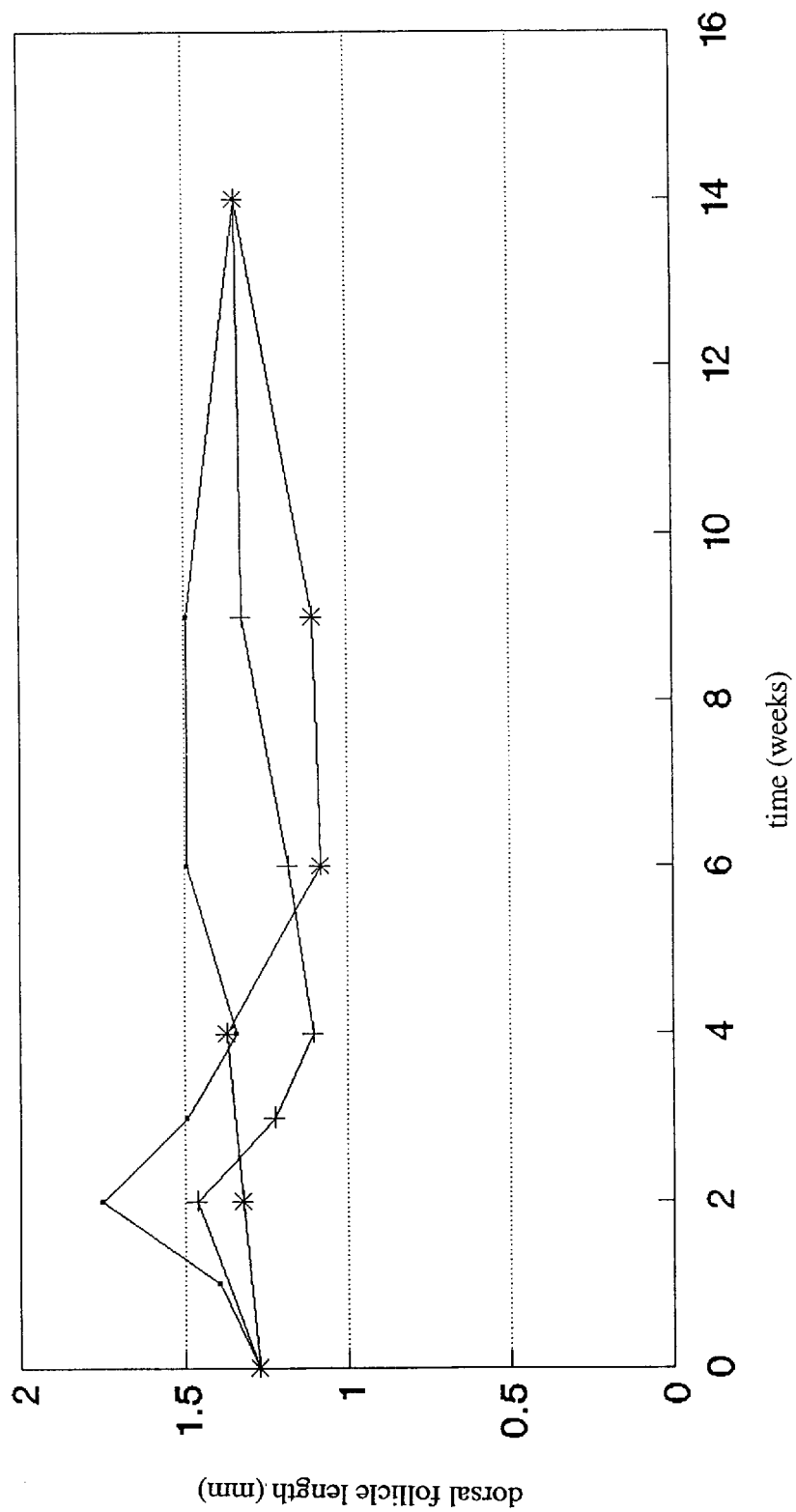
FIG. 1 is a graph showing follicle length of dorsal skin biopsies of hairless rats versus time in weeks after oral or topical administration of fenbendazole. The "dot" symbol represents follicle length observed microscopically in a dorsal skin biopsy of a hairless rat after oral administration of fenbendazole. The "plus" symbol represents follicle length observed microscopically in a dorsal skin biopsy of a hairless rat after topical administration of fenbendazole. The "asterisk" symbol represents follicle length observed microscopically in a dorsal skin biopsy of a negative control hairless rat untreated with fenbendazole.

A method for promoting keratinization on the body of an animal or human, particularly hair, nail, or skin keratinization, is provided. In accordance with the method, a therapeutic amount of a benzimidazole composition sufficient to cause keratinization is administered either systemically or directly to the site on the body at which keratinization is desired.

Keratin is a scleroprotein or albuminoid found predominantly in epidermis cuticular structures such as hair, nails, and horns. The term "keratinization" as used herein is defined as keratin formation or growth of all keratinizing structures and includes, but is not limited to, skin re-epithelialization, especially after first or second degree burns of the skin on the body of humans and animals, hair growth and regrowth from existing hair follicles, both in length and thickness, and the cornification or growth, both longitudinally and in thickness, of fingernails, toenails, claws, horns, hooves, and antlers. Keratinization, or the promotion of keratinization, results in the production of thicker, stronger and longer keratin structures. The method does not cause the production of new hair follicles, but causes the growth of preexisting follicles wherein miniaturized hairs become longer and thicker and may even develop pigmentation.

The term "hair growth" as defined herein includes the promotion and maintenance of normal active (anagen) hair growth following disruption of the hair growth cycle in any stage such as occurs when various chemotherapeutic drugs are administered or caused by telogen effluvium, conversion of hairs from vellus hairs to terminal hairs, an increase in hair shaft length, an increase in hair shaft diameter, an increase in hair shaft medullation, an increase in hair pigmentation, an increase in hair follicle length. The term "hair growth" further includes improved hair growth, enhanced hair growth, and restoration to normal hair growth.

The term "animal" as used herein refers to both human and non-human species, particularly mammals, and includes, but is not limited to, domestic, productive, and breeding animals such as dogs, cats, cattle and other ruminants, horses, sheep, goats, pigs, camels, alpacas, llamas, water buffalo, donkeys, rabbits, fallow deer, reindeer and similar mammals; pelt animals such as mink, foxes, chinchilla and raccoons; avian species or poultry such as chickens, geese, turkeys, pigeons, ducks, and ostriches; and animals such as reptiles and amphibians.

The terms "keratinization composition" and "keratinization promoting composition" as used herein include human and veterinary pharmaceutical, treatment, cleansing, and cosmetic compositions for administration to humans or animals.

Although not wishing to be bound by the following, a proposed mechanism of action of benzimidazoles to promote keratinization involves a blockage or interference with the effects of androgens, such as testosterone and its metabolites, on the epidermal cells of the outer root sheath of hair follicles, possibly by interactions such as inhibition of cytochrome P-450 isozymes such as P-450IA1 in human keratinizing structures, and P-450IA1, P-450IIA1, and P-450IIB1 in rat keratinizing structures. It is believed that the benzimidazole effectively opposes a genetic predisposition for premature miniaturization of hair follicles occurring during alopecia, particularly androgenic alopecia. Therefore, the method described herein includes the administration of compounds having the functional characteristics of benzimidazoles, namely cytochrome P-450 isozymes inhibitors, to inhibit the adverse effects of androgens on hair growth, such as alopecia, particularly androgenic alopecia.

The method is useful for the treatment of a wide variety of hair loss disorders in animals such as alopecia, including human androgenic alopecia of females and male pattern baldness; hair loss due to telogen effluvium, hair loss due to anti-cancer chemotherapy, oral or subcutaneous contraceptives and other drugs; hair loss due to topical chemical treatment, such as hair dyes, permanent wave solutions, and straighteners; and hair loss due to disease, such as leprosy or syphilis; illness; allergy; and hair follicle infection. The method is used either prior to anticipated hair loss, such as before or during the administration of anti-cancer chemotherapeutic drugs or after an observation or diagnosis of hair loss has been established. In addition, the method directly promotes faster, early onset of hair regrowth in humans or other mammals suffering from disorders such as telogen effluvium.

The method is also useful for hair or fur loss disorders in animals caused by disease, diet, metabolic disorders, insect bites, infection of follicles, allergies, and hot spots or other hair or fur erosions caused by excessive biting, chewing and scratching. In addition, the method is useful for improving or enhancing the growth or thickness of normal hair or fur.

Furthermore, the method is useful for enhancing, improving or restoring the normal strength, thickness, and length of normal, abnormal, or diseased nails, including fingernails and toenails in humans, and claws, horns, hooves and antlers in animals. Nails, defined herein to include fingernails, toenails, claws, horns, hooves and antlers, treated in accordance with the present method are less susceptible to bending, cracking, peeling and breaking. Therefore, the method is useful for the treatment of onychoschizia, also known as lamellar dystrophy, which is the horizontal separation of the corneocytes on the nail. The method is particularly useful for treating the hooves of horses, especially race horses, to enhance the strength and thickness of the hoof to prevent or inhibit cracking, breakage, and fissuring, and in addition to prevent pain and infection.

Nails treated in accordance with the present method are also less likely to show pitting of their surfaces after treatment. Therefore, the method is useful for the treatment of psoriasis of the nail bed, which causes nail pitting and deformation. The administration of a benzimidazole for the treatment of psoriasis of the nail bed may be in combination with other psoriasis treatments, such as the administration of methotrexate. In cases of severe psoriatic onychodystrophy, the remaining keratinous matter is first removed, such as by applying 20% urea in a hydrolytic base. After the nail bed is cleared, corticosteroids may be administered in combination with the benzimidazole.

By promoting normal to increased keratinization, the method described herein will allow a more economical production of keratin products such as wool, hides, pelts and horns.

The method is also useful to improve or enhance the rate or extent of wound healing by promoting the propagation of epidermal cells either in vivo or in vitro for subsequent transfer, or skin graft, to a patient suffering from a disorder such as trauma, burns, especially accident-induced burns, abraded skin, ulcers, congenital malformations, or surgery, in which large areas of skin must be generated. In addition, the method is useful for treating incised skin present from surgical procedures including incision by scalpel blades; vaporization of skin by various types of laser emitted energy, such as caused by laser surgery; necrotic skin secondary to cryosurgical procedures or ionizing radiation induced burns caused by an external beam such as cobalt radiation; or skin necrosis due implant radiation caused by cesium pellet implants.

Techniques have been developed for skin replacement in which autologous epidermal cells are propagated in vitro and applied to the skin of the patient from whom the cells were harvested. Such techniques are known to those skilled in the art. For example, epidermal cells can be impregnated in a matrix, such as a collagen matrix, to produce skin of a predetermined size or shape to be used for skin grafting.

The method described herein is additionally useful to combat cutaneous fungal infections, particularly fungal infections of the nails and skin such as dermatophytes and candidiasis by topical application of the benzimidazole composition to the nail or skin surface. Fungal infections, including fungal infections of the nails, are particularly prevalent in patients suffering from AIDS. The method demonstrates antifungal effects not only because benzimidazole compounds possess chemical fungicidal properties, but also because benzimidazoles promote keratinization, which allows outgrowth of the infected keratinized structure away from the body, thereby preventing or decreasing contact of the fungal elements with the newly developing keratinized structures on which the fungus depends for survival. Therefore, the promotion of keratinization contributes greatly to the fungistatic effect.

Benzimidazole Compounds

The term "benzimidazole" as used herein is a chemical compound containing a bicyclic ring structure in which benzene is fused to the 4- and 5-positions of an imidazole and includes benzimidazoles, benzimidazole carbamates, benzimidazole prodrugs, benzimidazole derivatives, and benzimidazole metabolites. Phenylguanidines are specifically included as suitable benzimidazole prodrugs: Amorphous, crystalline and granular benzimidazole compositions are included in the present definition of the term "benzimidazole". Benzimidazoles having minimal toxic side effects are preferred. Carbamates and, in particular, benzimidazole carbamates are used and can be used in large dosages because they have exhibited a low incidence of side effects.

The preferred benzimidazole compounds are benzimidazole anthelmintics. Anthelmintics are compounds useful for treating helminthiasis in humans and animals. The term "benzimidazole anthelmintic" is defined herein as any benzimidazole-containing agent known to act as a broad spectrum anthelmintic against endoparasites or nematodes such as ascarids, hookworms, whipworms, roundworms and kidneyworms. An analysis of the structure-activity relationships of numerous benzimidazole compounds is provided in the scientific article of Loewe and Urbanietz, Fenbendazole. I. Structure-Activity Relationships, *Pestic. Sci.* 8:544–549 (1977), which is incorporated by reference herein. The anthelmintic mechanism of action of benzimidazoles compounds appears to involve inhibition of the polymerization of tubulin into microtubules within various helminth species. It is understood that one skilled in the art would be able to screen benzimidazoles for anthelmintic activity, and thereby screen for keratinization promoting activity, using standard assays and techniques.

The preferred benzimidazole compound for use in the present method includes, but is not limited to, albendazole (SmithKline Beecham Pharmaceuticals, Philadelphia, Pa.), cambendazole (Merck/Univet, Rahway, N.J.), ciclobendazole (Janssen/Cilag, Titusville, N.J.), fenbendazole (Hoechst-Roussel Agri-Vet, Sommerville, N.J.), flubendazole (Janssen, Titusville, N.J.), luxabendazole (Hoechst-Roussel Agri-Vet, Sommerville, N.J.), mebendazole (Janssen, Titusville, N.J.), oxfendazole (Coopers/Syntex, Palo Alto, Calif.), triclabendazole (Ciba-Geigy, Summit, N.J.), oxibendazole (SmithKline Beecham/Univet, Philadelphia, Pa.), parbendazole (SmithKline Beecham/Ciba-Geigy, Philadelphia, Pa./Summit, N.J.), ricobendazole (Robert Young & Co., Wethersfield, Conn.), thiabendazole (Merck, Rahway, N.J.), and metabolites, derivatives, and prodrugs thereof, including the prodrugs febantel (Coopers/Bayer, Shawnee Mission, Kan.), netobimin (Schering Corporation, Kenilworth, N.J.), and thiophanate (Micro-Biologicals/RMB Animal Health). These benzimidazoles are or have been commercially available from the companies listed above in parentheses. The most preferred benzimidazoles are fenbendazole and prodrugs thereof; the sulfoxide metabolites of fenbendazole, such as oxfendazole; and the (4' hydroxyphenyl) thio metabolites of fenbendazole.

Fenbendazole has been described in European Patent Application Publication No. 090,368 to Ganley et al. for administration to animals to treat helminthiasis. Ganley et al. state that fenbendazole is non-teratogenic and non-carcinogenic and therefore safely used in animals at any stage of pregnancy. In addition, Ganley et al. claim that the drug has no adverse effect on fertility, and can be used at the time of conception in the female and the breeding male mammal and has no toxic or teratogenic effects on embryos or developing fetuses. Ganley et al. further describe fenbendazole as having a very high safety margin and is non-toxic to the humans who are administering the drug to animals. According to Ganley et al., oxfendazole and albendazole have substantially the same spectrum of activity as fenbendazole, but a lower therapeutic index. In addition, in avian species, fenbendazole fails to depress egg production or hatchability indices.

A list of the foregoing benzimidazoles, including the phenylguanidine prodrugs, and one or more chemical names commonly associated therewith, if available, are provided below:

albendazole: methyl 5-(propylthio)-1H-benzimidazol-2-yl carbamate, 5-n-propylthio-2-carbomethoxy-aminobenzimidazole, or methyl 5(6)-n-propylthio-2-benzimidazole carbamate cambendazole: isopropyl 2-(4-thiazolyl)-1H-benzimidazol-5-yl carbamate ciclobendazole (or cyclobendazole): methyl 5-cyclopropylcarbonyl-1H-benzimidaz-2-yl carbamate or 5-cyclopropylcarbonyl-2-carbomethoxyaminobenzimidazole fenbendazole: methyl 5-(phenylthio)-2-benzimidazolecarbamate or methyl [5-(phenylthio)-1H-benzimidazol-2-yl]carbamate, methyl 5(6)-phenylthio-1H-2-carbomethoxyaminobenzimidazole, or 5(6)-phenylthio-2-benzimidazole carbamate flubendazole: methyl 5-(4-fluorobenzoyl)-1H-benzimidazol-2-yl carbamate or 5-(4-fluorobenzoyl)-2-carbomethoxyamino-benzimidazole mebendazole: methyl N-(5-benzoyl-2-benzimidazolyl) carbamate or methyl 5-benzoyl-1H-benzimidazol-2-yl carbamate or 5-benzoyl-2-carbomethoxy aminobenzimidazole oxfendazole: methyl 5(6)-(phenylsulfinyl)-1H-benzimidazol-2-yl carbamate or 5-phenylsulfinyl-1H-2-carbomethoxyaminobenzimidazole oxibendazole: methyl 5-(1-propoxy)-1H-benzimidazol-2-yl carbamate or 5-propoxy-2-carbomethoxy aminobenzimidazole parbendazole: methyl 5-(1-butyl)-1H-benzimidazole-2-yl carbamate or 5-(1-butyl)-2-carbomethoxy aminobenzimidazole thiabendazole: methyl 2-(4-thiazolyl)-1H-benzimidazole or 4-(2-benzimidazolyl)thiazole or 2-(4-thiazolyl)-1H-benzimidazole triclabendazole: 6-chloro-5-(2,3-dichlorophenoxy)-2-methylthiobenzimidazole or 5-chloro-6-(2,3-dichlorophenoxy)-2-methylthio-1H-benzimidazole febantel: [2-[(methoxyacetyl)amino]-4-(phenyl-thio)] phenyl carbonimidoyl]biscarbamic acid dimethyl ester or dimethyl [[2-(2-methoxyacetamido)-4-(phenylthio) phenyl]-imidocarbonyl]dicarbamate netobimin: 2-[[[(methoxycarbonyl)amino][[2-nitro-5-(propylthio)phenyl]amino]methylene]amino] ethanesulfonic acid or 2-[[[(methoxycarbonyl)amino][[2-nitro-5-(propylthio) phenyl]imino]methyl]amino] ethanesulfonic acid or methyl [N'-[2-nitro-5-(propylthio) phenyl]-N-(2-sulfoethyl)amidino]carbamate or N-methoxycarbonyl-N'-[2-nitro-5-(propylthio)phenyl]-N"-2-(ethylsulfonic acid)guanidine thiophanate: [1,2-phenylenebis(iminocarbonothioyl) biscarbamic acid diethyl ester or 4,4'-o-phenylenebis[3-thioallophanic acid]diethyl ester or 1,2-bis(3-ethoxycarbonyl-2-thioureido)benzene Benzimidazoles useful in the method and composition described herein include compounds having one or more of the formulas set forth below as Formula 1, Formula 2 or Formula 3 and pharmaceutically acceptable salts thereof. Preferred benzimidazoles for use in the compositions and methods described herein have one or more of the formulas set forth as Formula 2. Most preferred benzimidazoles for use in the compositions and methods described herein have one or more of the formulas set forth as Formula 3. As described in more detail below, the compounds are most preferably provided in an amorphous (non-crystalline) form to enhance solubility.

Formula 1:

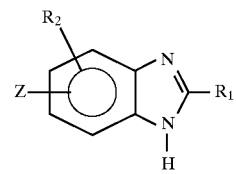

wherein Z is —H or halo; $R_1$ is a five-membered heteroaromatic ring containing 1, 2, or 3 heteroatoms selected from O, N, and S, or $R_1$ is —SCH$_3$, —NHCOOR$_3$, —NHCSOR$_3$, or —NHCOSR$_3$ where $R_3$ is alkyl, cycloalkyl, alkenyl, alkynyl, phenyl, or naphthyl; and $R_2$ is —H, R, or —XR, where X is O, S, SO$_3$, O$_3$S, —C(O), or —NHCOO—; and R is alkyl, cycloalkyl, aryl or aryl-alkyl, optionally substituted with halo, alkyl, hydroxy, or alkoxy.

Formula 2:

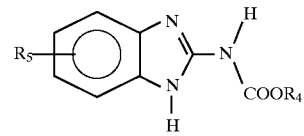

wherein $R_4$ is lower alkyl; and $R_5$ is —S(O)$_m$R$_6$, —OR$_6$, or —Y$_1$(CH$_2$)$_n$Y$_2$R$_7$ where $Y_1$ and $Y_2$ are each independently O, S, or S(O), $R_7$ is lower alkyl, phenyl, or naphthyl, and n is 1, 2, 3, or 4; $R_6$ is lower alkyl, cycloalkyl, alkenyl of 3 to 7 carbon atoms, alkynyl of 3 to 7 carbon atoms, phenyl, benzyl, phenylethyl, or naphthyl; and m is 0 or 1.

Formula 3:

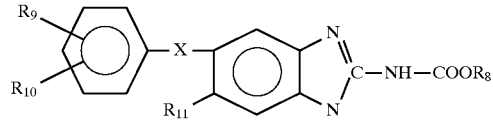

wherein $R_8$ is an alkyl of 1 to 4 carbon atoms, $R_9$ and $R_{10}$ are, independently, hydrogen, hydroxyl, alkoxy having 1 to 4 carbon atoms, halogen, trifluoromethyl, alkyl having 1 to 4 carbons atoms and carbalkoxy having 1–5 carbon atoms in the alkoxy group, $R_{11}$ is hydrogen or chlorine, fluorine, bromine, or iodine and X is oxygen, sulfur, sulfoxide or sulfonate ester.

Combinations of compounds of Formulas 1, 2 and 3 are also useful. A preferred combination contains amorphous compounds of Formula 1 or a combination of an amorphous compound of Formula 1 and an amorphous compound of Formula 2, especially where $R_4$ is methyl. In a preferred class of compounds of Formula 2, $R_5$ is $SR_6$ or $S(O)R_6$, and most preferably $R_6$ is phenyl or n-propyl. Especially preferred combinations contain the compound fenbendazole, most preferably in combination with oxfendazole or triclabendazole.

The term "alkyl" as used herein is a saturated hydrocarbon radical containing 1 to 20 carbon atoms. The term "lower alkyl" as used herein is an alkyl radical of 1 to 6 carbon atoms. The term "cycloalkyl" as used herein is a cyclic saturated hydrocarbon radical containing 3 to 8 carbon atoms. The term "alkenyl" as used herein is a hydrocarbon radical of 3 to 7 carbon atoms, containing a double bond. The term "alkynyl" as used herein is a hydrocarbon radical of 3 to 7 carbon atoms, containing a triple bond. The term "alkoxy" as used herein is a radical of the form RO—, where R is lower alkyl or cycloalkyl as described above. The term "aryl" as used herein is an aromatic hydrocarbon radical containing 6 carbon atoms, also known as a phenyl ring. The term "aryl-alkyl" as used herein is an aryl group to which a lower alkyl group, as described above, is attached. The term "halo" as used herein is a halogen radical such as fluoro, chloro, bromo, or iodo.

Benzimidazoles to be used in the present method for promoting keratinization may be obtained commercially or synthesized by conventional methods known in the art, such as by methods set forth in U.S. Pat. Nos. 3,928,375 and 3,954,791, which are incorporated by reference herein and in the article by Townsend and Wise entitled "The Synthesis and Chemistry of Certain Anthelmintic Benzimidazoles", *Parasitology Today* 6:107–112 (1990), which is incorporated by reference herein.

Methods of Administration and Formulations

The benzimidazole compound, in granular, crystalline, powder, or amorphous form, is provided in combination with a suitable solvent or carrier as a benzimidazole composition for administration to a human or animal. The benzimidazole composition is given systemically by oral administration or is given locally by injection or topical application for parenteral absorption. Topical application includes transdermal or percutaneous delivery such as by application of a percutaneous occlusive patch. The preferred method of administration is topical.

Topical administration should be directed to the site where keratinization is most likely to occur. The site of keratinization in the skin is the epidermis. The site of keratinization in hair or fur is the follicle. Therefore, for topical treatment of alopecia, the benzimidazole composition should be applied to the bald regions of the scalp or skin. Topical treatment of nail disorders should be applied at the cuticle base of the nail to maximize drug concentration in the vicinity of the keratogenous zone, which lies beneath the lunula, or "white moon" shape at the base of the nail. The locations of these portions of the nail are well known to those skilled in the art and are described in dermatology texts such as on pages 557–559 of the dermatology text HANDBOOK OF NON-INVASIVE METHODS AND THE SKIN, J. Serup and G. B. E. Jemac, eds., CRC Press, Boca Raton, Fla., 1995.

For topical administration, the benzimidazole, benzimidazole prodrug, benzimidazole metabolite or benzimidazole derivative is dissolved, suspended or mixed as a paste, cream or gel in an appropriate solvent, homogenate, or carrier, such as a pharmaceutically acceptable or cosmetically acceptable carrier, to form a benzimidazole composition. It is known by those skilled in the art that conventional benzimidazole preparations are rarely soluble in many pharmaceutically acceptable carriers and are nearly insoluble in aqueous solutions. Therefore, the formulation may be prepared in an oil or oil-in-water emulsion. Suitable oils include, but are not limited to, arachis oil, peanut oil, olive oil, sesame oil, castor oil, corn oil; synthetic triglycerides; and soluble polymers. The carrier or diluent may also include a delayed release material, such as glyceryl monostearate or glyceryl distearate alone or in combination with a wax. The composition may additionally contain conventional agents such as preservatives (including antioxidizing agents such as tocopherol), thickening agents, wetting and dispersing agents, buffers, humectants, such as lactic acid and glycolic acid copolymers, emulsifying agents, fillers, emollients and surface active agents (such as sorbitane fatty acid esters).

Alternatively, the benzimidazole of a topical formulation is dissolved or suspended in an aqueous suspension containing benzyl alcohol, polyoxyethylene sorbitan monooleate, ethoxylated sorbitane fatty acid esters, aprotic polar solvents, and, optionally, thickeners such as propylene glycol, polyethylene glycol, monohydric alcohol, n-methyl pyrrolidone, carboxymethyl cellulose, such as Methocel® A-15 Premium Carboxymethyl Cellulose (Dow Chemical Co., Midland, Mich.) or other appropriate polymers. In addition, solvents such as dimethylsulfoxide (DMSO), DMSO glycol, decylmethylsulfoxide (decyl-MSO), dimethylacetamide (DMA), dimethylformamide (DMF), saturated fatty acids such as lauric acid and alcohols, and weak surfactants containing a moderately sized polar group such as 1-dodecyl-azacyclohepten-2-one (Azone®, E. L. Nelson), alcohols and ketones, particularly acetone, are useful for dissolving or partially dissolving the compound to enhance skin penetration of the benzimidazole. The penetration enhancement of benzimidazoles by saturated fatty acids may be maximized when propylene glycol is used as the vehicle.

An additional topical benzimidazole formulation for enhanced skin penetration employs the combined administration of cyclodextrins, such as carboxymethylethyl-β-cyclodextrin and a lipophilic penetration enhancer such as HPE-101 (1-[2-decylthio)-ethyl]aza-cyclopentane-2-one) or 1-dodecyl-azacyclohepten-2-one (Azone®) in a topical vehicle.

For simplicity and ease of use for topical administration to the body, the benzimidazole composition contains the benzimidazole compound in combination with a cosmetic, treatment, or cleansing hair or nail preparation such as a hair shampoo, hair rinse, hair conditioner, hair spray, hair mousse, hair gel, nail lotion, nail ointment, nail paste, nail polish or nail polish remover.

Concentrated preparations containing a benzimidazole in a concentration of 0.5 to 90 percent by weight, preferably 5 to 50 percent by weight, may be prepared and diluted before administration. The preferred concentration to be administered topically is preferably from 5 to 50 mg benzimidazole per kilogram body weight. Particularly preferred concentration employed are from 10 to 30 mg benzimidazole per kilogram body weight. A most preferred administration concentration is 25 mg benzimidazole per kilogram body weight.

Poorly water-soluble drugs such as benzimidazoles exhibit increased bioavailability when dispersed in a non-aqueous mixture of a surfactant and a co-solvent in the presence of heat as described in U.S. Pat. No. 5,169,846 to Michael J. Crooks, which is incorporated by reference herein. Formulations produced by the method of Crooks are described as being free-flowing and completely miscible with water and may be well suited to topical administration.

Amorphous benzimidazoles are preferred over crystalline or granular forms, particularly for topical administration, due to their enhanced solubility in a variety of solvents. In addition, the amorphous benzimidazoles have a higher bioavailability and efficacy than crystalline benzimidazoles. Amorphous benzimidazole derivatives are prepared as described in European Patent Application Publication No. 224,249 to Richard Allen Runkel, which is incorporated by reference herein. Basically, the amorphous compounds are produced by precipitating a benzimidazole derivative from an acidic or basic solution by rapidly adding an amount of base or acid sufficient to adjust the solution to the pH of lowest benzimidazole solubility or by rapidly precipitating a benzimidazole derivative from an acid or basic solution by adding a basic or acid solution containing a stabilizing amount of a stabilizer polymer. Stable amorphous compositions contain an amorphous benzimidazole compound in combination with a stabilizing amount of a stabilizing polymer such as cellulose derivatives, polyvinyl pyrrolidone and derivatives, xanthan gums, pectins, alginates, tragacanth and derivatives, gum arabic and derivatives, carrageenans, agar and derivatives, polysaccharides from microbial sources, arabinogalactans, galactomannans, and dextrans. The most preferred stabilizing polymer is a cellulose derivative such as methylcellulose, Methocel® A-15, Methocel® A4C, or carboxymethylcellulose. The stabilized amorphous benzimidazole compositions are appropriate for administration topically or by parenteral injection In addition, the stabilized amorphous benzimidazole is useful in oral formulations such as suspensions, tablets, or top dressing crumbles specifically for mixing into animal feed or water as described in more detail below.

For oral administration, the benzimidazole compound may be combined with an orally ingestible carrier formed into tablets, capsules, powders, granules, pastes, homogenates, solutions, suspensions, emulsions, boli, medicated feed or added to drinking water. For delivery to animals, the benzimidazole composition is more easily administered when combined with feed or drinking water.

Oral solutions are prepared by dissolving, suspending or homogenizing the benzimidazole, benzimidazole prodrug, benzimidazole metabolite or benzimidazole derivative in a suitable solvent and, if appropriate, adding additives such as solubilizers, acids, bases, buffer salts, antioxidants and preservatives. The solutions may be filtered and packed under sterile conditions. Solvents that promote dissolution of the active compound in the main solvent or substances that prevent precipitation of the benzimidazole may be used as solubilizers. Examples of such solubilizers include polyvinyl pyrrolidone, polyoxyethylated castor oil, and polyoxyethylated sorbitan esters. When the benzimidazole is provided in an amorphous (non-crystalline) form, the preferred stabilizer is a stabilizer polymer as described in European Patent Application Publication No. 224,249 to Runkel. Exemplary preservatives include benzyl alcohol, trichlorobutanol, parahydroxybenzoic acid esters and n-butanol.

The benzimidazole may additionally be combined with conventional excipients and adjuvants such as starch, cellulose, talc, magnesium stearate, sugar, gelatin, calcium carbonate, silicic acid, carboxymethyl cellulose and the like. The compound may also be encapsulated within microparticles or incorporated into a monolithic matrix, for subsequent or sustained release. Microparticles may be made using synthetic polymers, natural polymers, proteins and polysaccharides, including phase separation, solvent evaporation, emulsification, and spray drying. Generally, polymers form the supporting structure of these microspheres, and the compound is incorporated into the polymer structure. Exemplary polymers used for the formation of microspheres include homopolymers and copolymers of lactic acid and glycolic acid (PLGA). It will be understood by those skilled in the art that microparticles, depending on their composition and size, may be administered orally, by injection, or topically.

An oral formulation is typically prepared by adding the additives to water and stirring until dissolved, then adding the benzimidazole and stirring until the mixture is homogenous. The mixture is passed through a homogenizer, if necessary, to obtain relatively uniform particle size distribution of approximately one micron. Homogenization is achieved by means known to those skilled in the art, such as with a rotor stator or high pressure homogenizer. When using a single head high pressure homogenizer, the mixture is passed through until the pressure can be maintained within the range of approximately 9,000 to 15,000 psig, preferably in a range of from about 12,000 to about 14,000 psig, most preferably within a range of about 13,000 psig. When using a triple head high pressure homogenizer, the mixture is passed through at a pressure of from about 2,000 to about 10,000 psig, preferably from about 4,000 to 8,000 psig.

The concentration of benzimidazole for oral administration is preferably between 0.5 and 50 mg per kilogram of body weight for a prolonged period of time. Generally, the compound is administered initially at a high concentration and the patient is then placed on a maintenance dosage indefinitely. An alternative preferred concentration for oral administration is between approximately 2 and 20 percent by weight for use on animals and between approximately 20 and 80 percent by weight for humans.

In avian species, such as chickens, pigeons, ducks and geese a 1% to 10% benzimidazole suspension in drinking water may be given for a seven day period of time every two to three weeks. A concentrated (about 10% to about 30%) benzimidazole formulation may be diluted with water to yield a benzimidazole concentration from approximately 4,000 ppm to 10,000 ppm, preferably from about 6,000 ppm to 10,000 ppm, most preferably about 8,000 ppm. This diluted formulation may be used as a stock solution that is further diluted, for example, one ounce of the stock formulation is diluted in approximately a 1:128 ratio to obtain medicated drinking water having a benzimidazole concentration of from about 45 to 80 ppm, preferably 65 ppm. Alternatively, the concentrated benzimidazole formulation is diluted directly to a concentration of from approximately 45 to approximately 80 ppm, preferably approximately 65 ppm and used for avian drinking water directly. The concentration of benzimidazole is calculated to provide the targeted amount of benzimidazole per body weight of the avian or poultry being treated, preferably in the range of approximately 1 mg to 5 mg of benzimidazole per kilogram of body weight per day in the volume of drinking water normally consumed by the animal being treated in a 6 to 12 hour treatment period, preferably an 8 hour treatment period.

It will be understood by those skilled in the art that the particular dose or formulation for either topical or oral administration will be determined in part by consideration of the animal or human undergoing treatment, the particular biological effects manifested by the benzimidazole and other components utilized in the formulation, and the extended period of time over which the effective treatment is desired.

The compositions and methods described above will be further understood with reference to the following non-limiting examples.

EXAMPLE 1

Oral and Topical Administration of Fenbendazole to Hairless Rats to Promote Hair and Claw Growth An experiment was performed to compare the effects of oral and topical administration of fenbendazole to hairless rats on hair and claw growth.

Experimental Procedure:

Circular dorsal skin biopsies (4 mm) were taken from adult CD® Albino Hairless rats (CR1:CD® (SD)-hrBR, Charles River Laboratories, Wilmington, Mass.) with a skin punch prior to either oral or topical administration of fenbendazole and at 7 day intervals thereafter for 35 days. Dorsal skin biopsies samples were also removed from a negative control rat who had received no fenbendazole either orally or topically. The biopsies were taken after administration of isoflurane anesthesia and analyzed microscopically by a dermatologic pathologist.

Topical Administration

Finely ground fenbendazole powder (22%, Hoechst-Roussel Agri-Vet, Sommerville, N.J.) was suspended to make a supersaturated solution in 100% acetone. The dorsal body of an adult hairless rat was treated topically by applying the fenbendazole suspension with a cotton swab each day for 30 days. The head and tail were not treated. The rat was not bathed, but was gently wiped with a damp cloth prior to each subsequent treatment to rid the test surface of granular debris.

Oral Administration

The fenbendazole powder was diluted (one teaspoonful in 30 ml water) to provide an 18 mg/ml aqueous solution and was placed in a water bottle. The rat consumed the entire contents of the water bottle in a 24 hour period, at which time a 30 ml aliquot of the fenbendazole solution was resupplied for a 30 day dosing period.

Results

The rat receiving fenbendazole orally exhibited hair growth on the face, lateral thorax and lateral abdomen by day 7. Hair growth on the face of this rat was patchy, straight and white. Hair growth on the lateral thorax and lateral abdomen of this rat was white, fine and crimped. The hair growth on the lateral auxiliary area was straight and white.

White hair was definitely visible on the rats treated orally and topically on the facial, ventral neck, foreleg circumferentially, hind leg circumferentially, tail region and paws by day 30 of treatment. The dorsum (where the skin biopsies were taken) exhibited only a small amount of hair growth. The muzzles of the treated rats contained long, crimped vibrissae. In addition, the claws on the treated animals showed a significant increase in length. Some hair growth was observed on the control rat in the same general areas as observed in the treated rats. However, the hair growth on the control rat was minimal and significantly less than that observed on the treated rats.

Upon microscopic examination, no measurable differences were observed between treated and control animal dorsal skin biopsy samples except for follicle length. A graph of follicle length in the treated and untreated animals over the thirty day treatment period is set forth in FIG. 1. Follicle length as measured microscopically is the longest distance from the granular layer of the epidermis to the base of the deepest follicle, measured vertically in millimeters. As shown in FIG. 1, both oral and topical fenbendazole administration resulted in an increase in follicle length that peaked at day 14, subsided and then increased gradually again from day 35 onwards. Follicle length of the biopsy removed from the rat who had received fenbendazole orally was higher than the control for all samples except the 28 day sample, which was the same for both the oral treatment and untreated rat. The follicle length of the biopsy taken from the rat who had received fenbendazole topically was always less than that of the orally treated rat, but was higher than the control on day 14 and days 42–63.

EXAMPLE 2

Oral Administration of Fenbendazole to Hairless Rats to Promote Hair and Claw Growth An experiment was performed to determined the effects on hair growth of an oral fenbendazole suspension administered to hairless rats.

Experimental Procedure:

Cylindrical dorsal skin punch biopsy specimens (4 mm diameter) were taken from the dorsal facial area and the right lateral thigh area of adult CD® Albino Hairless rats (CR1:CD® (SD)-hrBR, Charles River Laboratories, Wilmington, Mass.) at day 0 (prior to oral fenbendazole suspension administration), day 17 and day 29 (after oral fenbendazole suspension or control suspension administration). The skin punch biopsies were taken as described above in Example 1.

Thirty milliliters of a fenbendazole solution was prepared by mixing 1 teaspoonful of fenbendazole powder (22%, Hoechst-Roussel Agri-Vet, Sommerville, N.J.) in 30 ml of water to give a final concentration of 18 mg/ml. The fenbendazole solution was placed in separate water bottles for each of two rats receiving treatment. The rats consumed the entire contents of the water bottles in a 24 hour period, at which time a 30 ml aliquot of the fenbendazole solution was resupplied for a 30 day dosing period. A negative control rat received an equivalent quantity of water.

Results

The rats receiving fenbendazole orally daily for 30 days exhibited hair growth on the face, lateral thorax, lateral abdomen, and lateral thighs by day 7. The hair growth appeared white, patchy and straight on all areas listed. The muzzles exhibited long crimped to curling vibrissae by day 17. The claws on all four paws of the rats receiving fenbendazole showed significant growth in length, along with increased periungual fold keratinization around each claw.

Hair growth and claw length and attendant keratinization was minimal to absent on the negative control rat.

Figure 2:
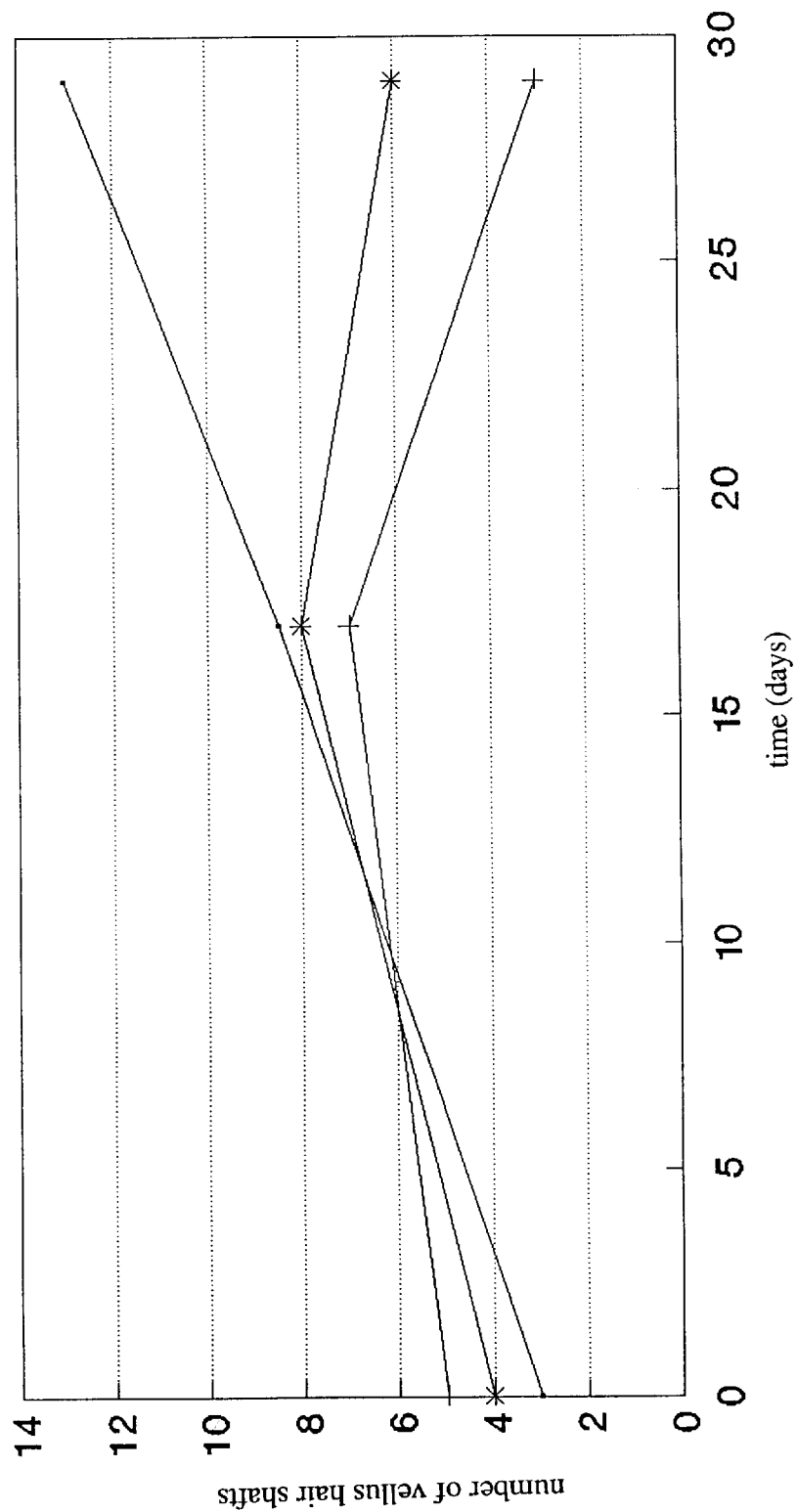
FIG. 2 is a graph showing the number of vellus hairs present on facial skin biopsies of hairless rats versus time in days after oral administration of fenbendazole. The "dot" symbol and the "asterisk" symbol represent the number of vellus hairs observed microscopically in facial skin biopsies of two hairless rats after oral administration of fenbendazole. The "plus" symbol represents the number of vellus hairs observed microscopically in a facial skin biopsy of a negative control hairless rat untreated with fenbendazole.
Figure 3:
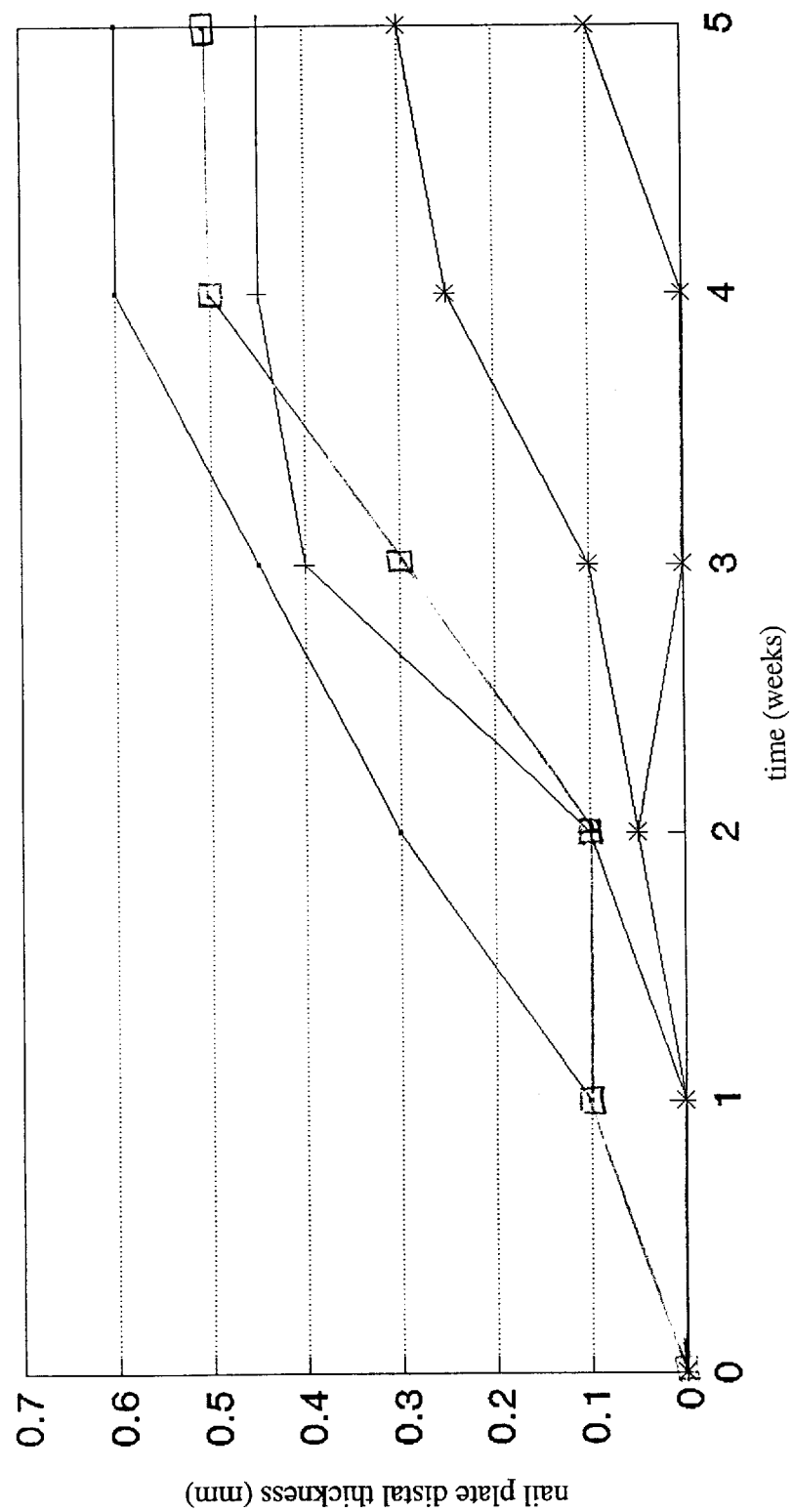
FIG. 3 is a graph showing nail plate distal thickness versus time in weeks of each finger of the left hand of human Female 1 receiving topical applications of fenbendazole to the nail. The "dot" symbol is the thumb. The "plus" symbol is the index finger. The "asterisk" symbol is the *digitus medius*. The "square" symbol is the *digitus anularis*. The "x" symbol is the *digitus minimus*.
Figure 4:
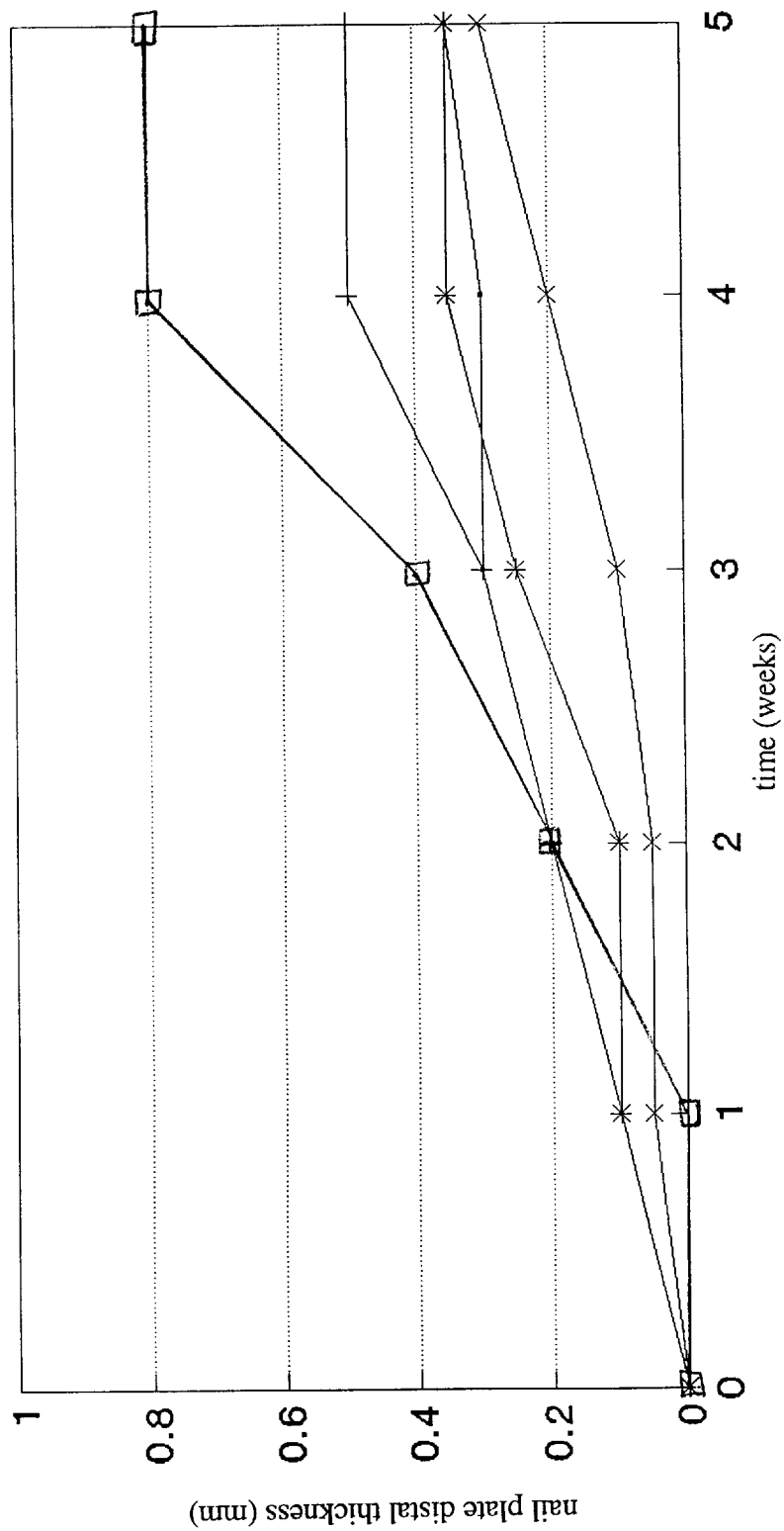
FIG. 4 is a graph showing nail plate distal thickness versus time in weeks of each finger of the left hand of human Female 2 receiving topical applications of fenbendazole to the nail. The symbols are the same as in FIG. 3.
Figure 5:
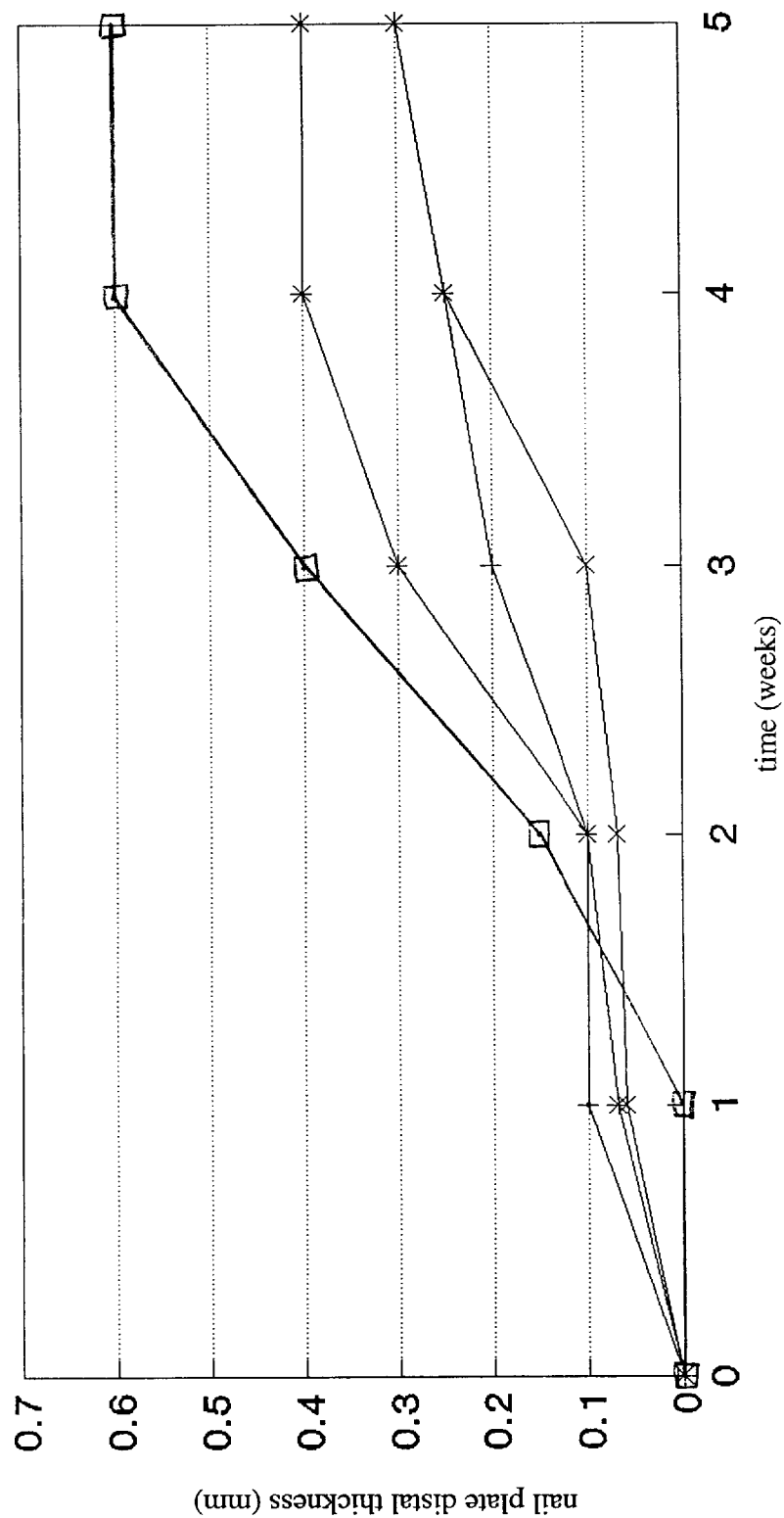
FIG. 5 is a graph showing nail plate distal thickness versus time in weeks of each finger of the right hand of human Female 1 receiving topical applications of fenbendazole to the nail. The symbols are the same as in FIG. 3.
Figure 6:
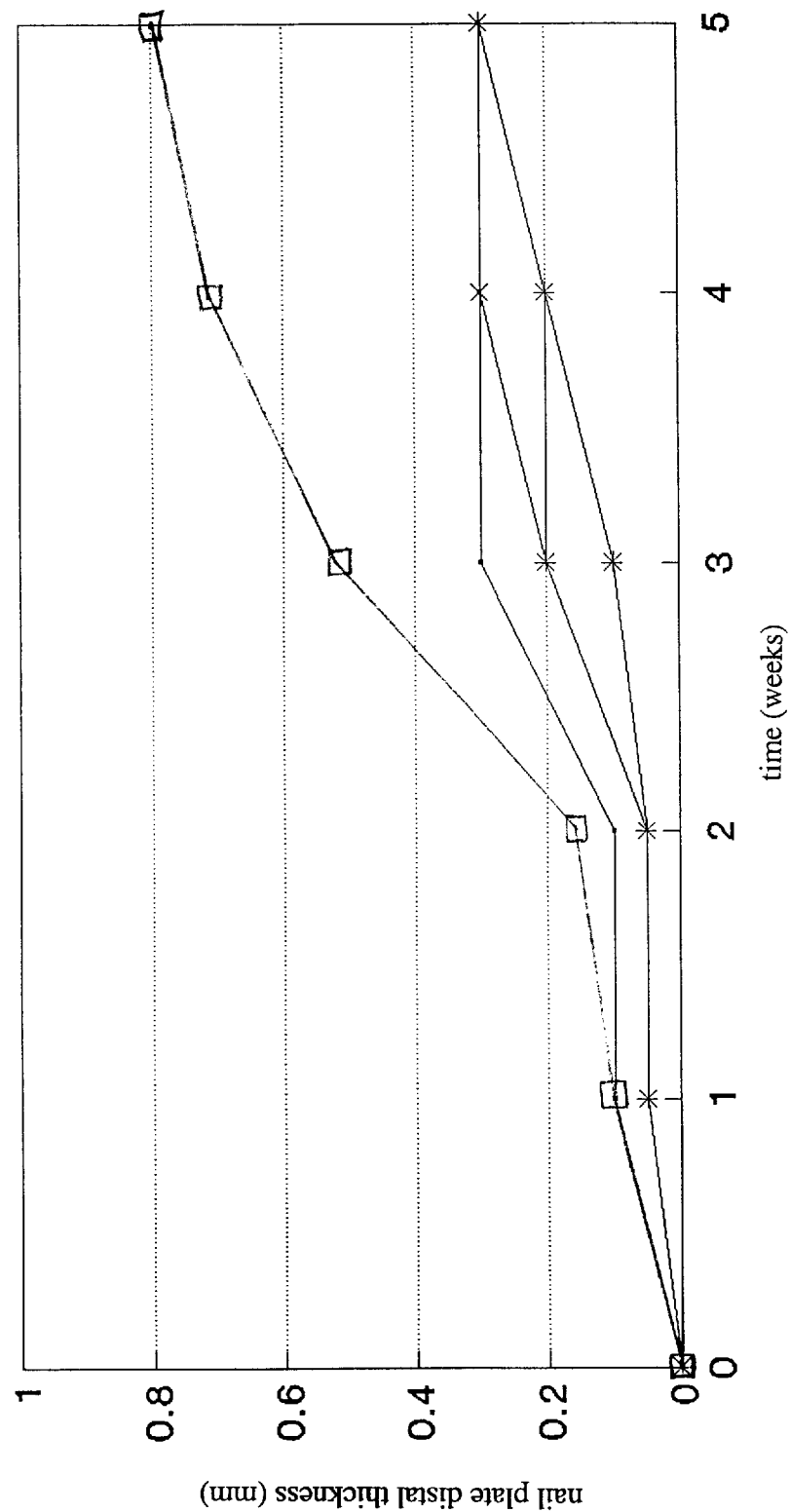
FIG. 6 is a graph showing nail plate distal thickness versus time in weeks of each finger of the right hand of human Female 2 receiving topical applications of fenbendazole to the nail. The symbols are the same as in FIG. 3.
Figure 7:
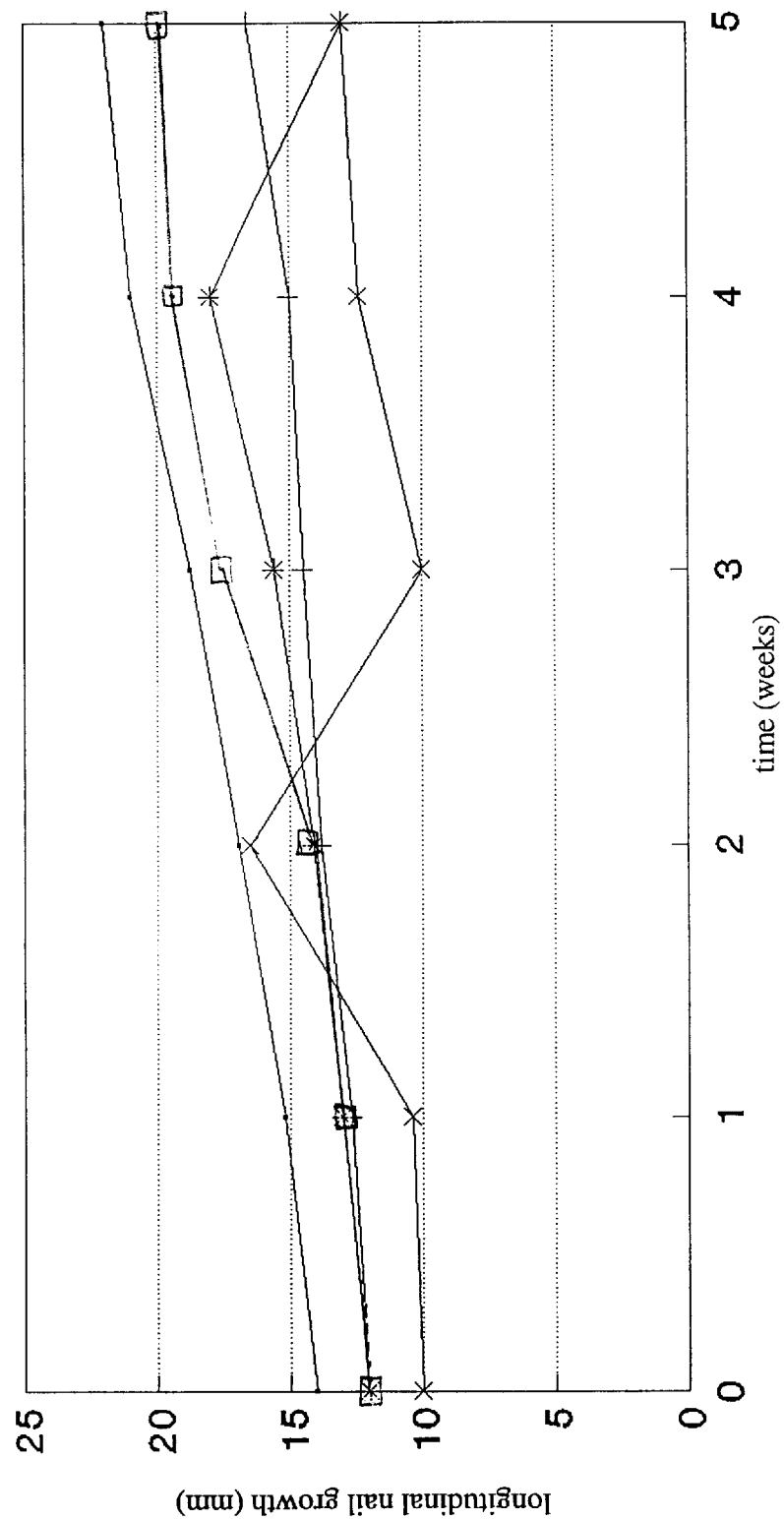
FIG. 7 is a graph showing longitudinal nail growth versus time in weeks of each finger of the left hand of human Female 1 receiving topical applications of fenbendazole to the nail. The symbols are the same as in FIG. 3.
Figure 8:
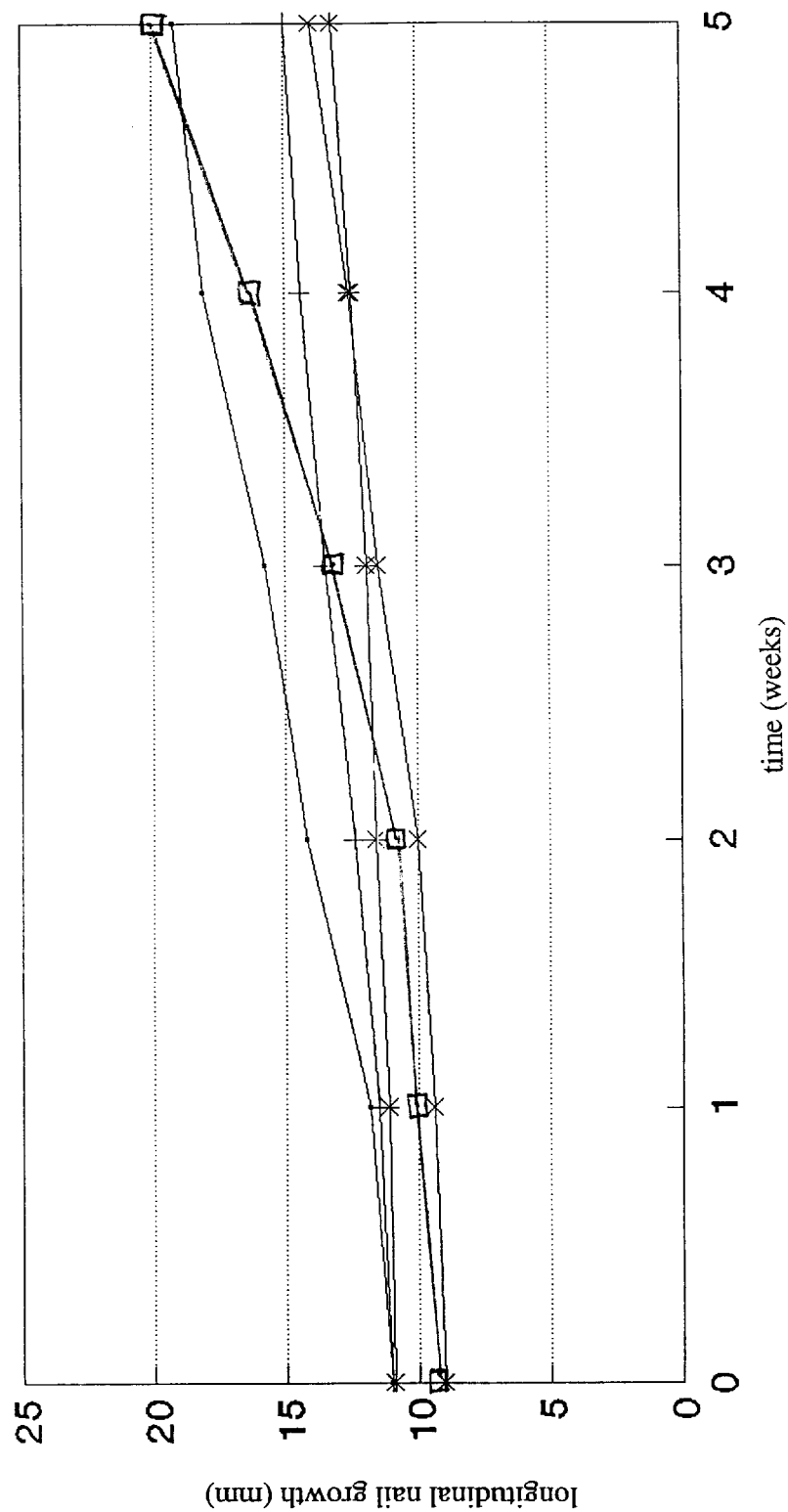
FIG. 8 is a graph showing longitudinal nail growth versus time in weeks of each finger of the left hand of human Female 2 receiving topical applications of fenbendazole to the nail. The symbols are the same as in FIG. 3.
Figure 9:
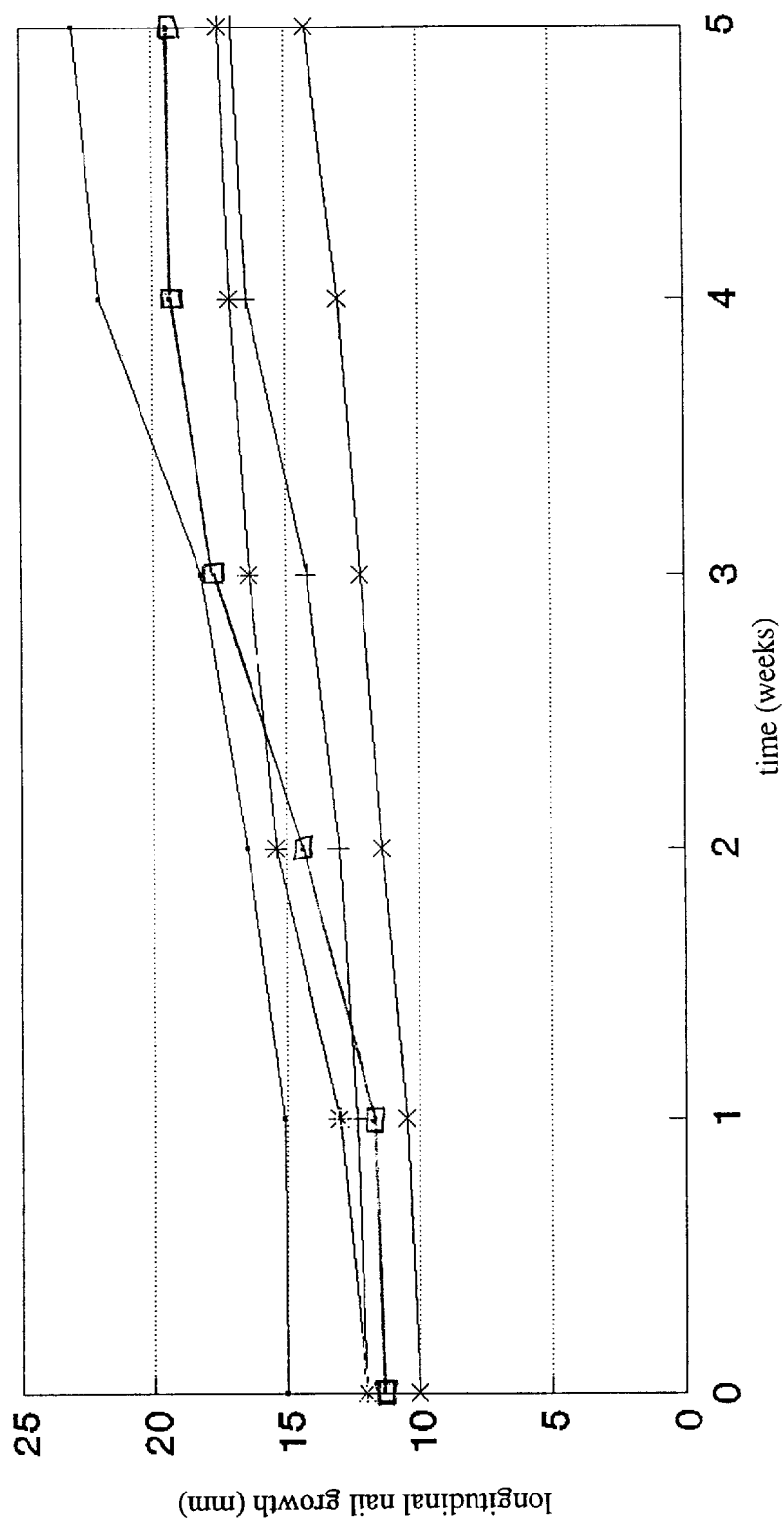
FIG. 9 is a graph showing longitudinal nail growth versus time in weeks of each finger of the right hand of human Female 1 receiving topical applications of fenbendazole to the nail. The symbols are the same as in FIG. 3.
Figure 10:
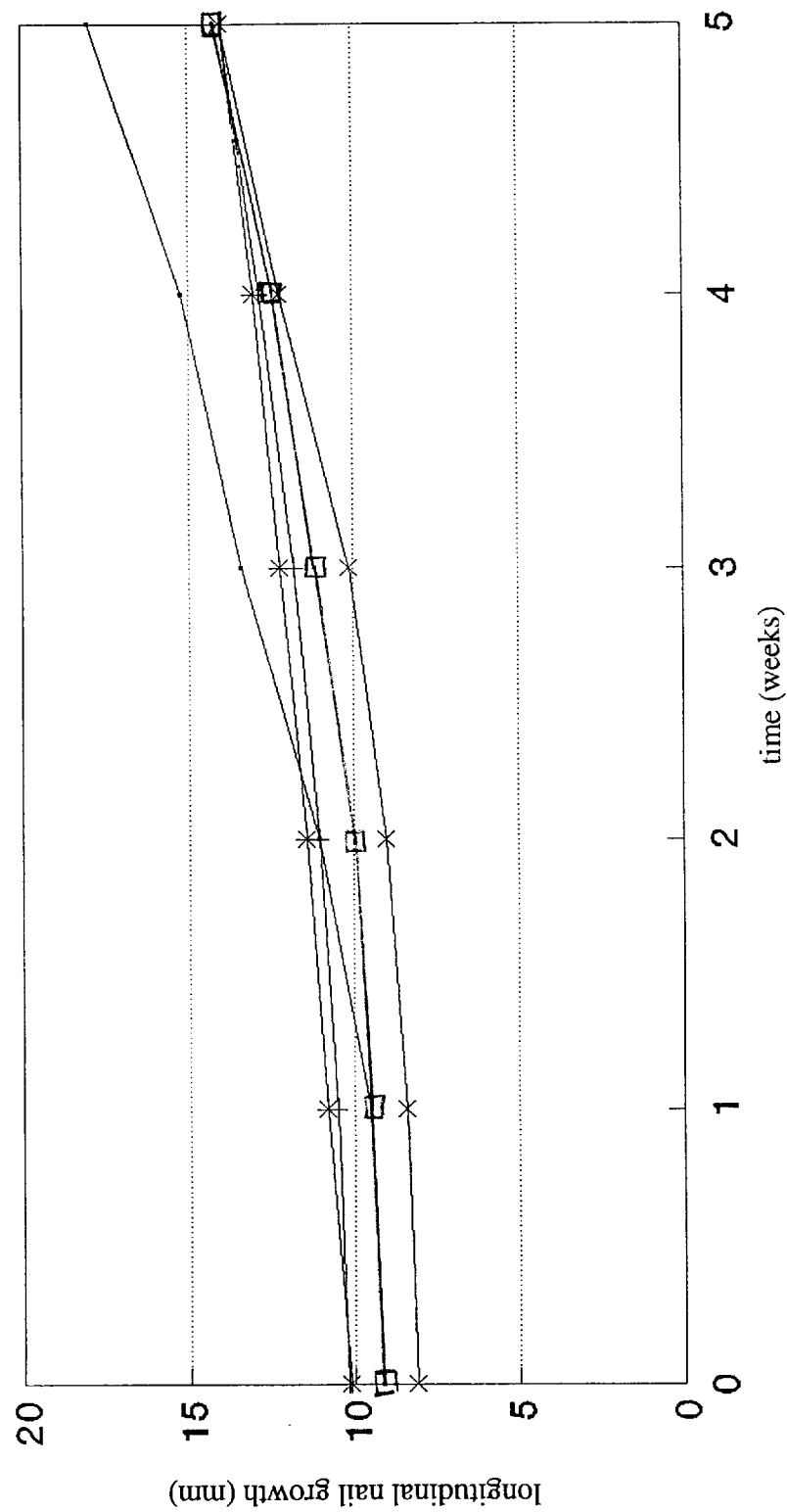
FIG. 10 is a graph showing longitudinal nail growth versus time in weeks of each finger of the right hand of human Female 2 receiving topical applications of fenbendazole to the nail. The symbols are the same as in FIG. 3.

Upon microscopic examination, no meaningful differences were observed between treated and control animal dorsal skin biopsy samples or follicle length. However, measurable differences were observed between treated and control animal facial biopsy samples for the number of vellus hair shafts. A graph showing the number of vellus hair shafts from samples taken from the facial areas in the treated and untreated animals over the 30 day treatment period is set forth in FIG. 2.

EXAMPLE 3

Topical Administration of Fenbendazole to Fingernails to Increase Nail Plate Thickness and Length An experiment was performed to determined the effects of topical fenbendazole administration on fingernail plate thickness and length.

Experimental Procedure:

Three teaspoonsful of finely ground fenbendazole powder (22%, Hoechst-Roussel Agri-Vet, Sommerville, N.J.) was combined with 15 ml of 90% dimethylsulfoxide (DMSO)

and mixed well. The solution was applied topically with a dropper and massaged gently into the uncut cuticular and proximal nail fold surfaces of dry, clean, fingernails of each finger of two human adult females.

Prior to treatment, the fingernails of the subjects exhibited a slow growth rate and short length, primarily due to chronic breakage horizontally at the quick or distal portion of the nail. Nail breakage was associated with soft, easily bent nails or horizontal splitting or flaking as the nails grew away from the nail bed. All nails were cut back to the nail bed to allow for confluent nail growth and equality of growth among fingernails during the course of treatment. The first measurement was taken on day 0. The fenbendazole solution was applied from day 1 to day 14. Subsequent measurements were taken on days 7, 14, 21, 28, and 35.

All fingernails demonstrated relief from onychoschizia during and after treatment. Nail thickness was maintained and progressively increased during the 35 trial period. All nails failed to show signs of fragility, such as bending when digital pressure was applied to the fingernail, and failed to exhibit pitting, nail layer separation, or horizontal flaking as the nails grew longitudinally away from the nail bed edge.

Nail plate thickness of all 10 fingernails was measured at 7 day intervals with a stainless steel caliper at the central aspect of the free edge of the nail plate as the nail plate emerged over the nail bed. The caliper was positioned to grip the free edge of the fingernail using standardized pressure. Measurements were made in fractions of a millimeter. At the time of measurement, all nails were clean and dry without the presence of other nail treatment, polish, or cleanser. The caliper was positioned so that artifacts could not be produced by angling the caliper.

Longitudinal growth of each nail plate was measured with a straight ruler in sub-millimeter increments, viewed by use of a magnifying loupe of 10× magnification.

The results for each fingernail of each experimental subject, human female 1 and human female 2, are shown in Tables 1–4 below and presented in graphical form in FIGS. 3–10. All measurements are in millimeters. The results for each subject are separated by a slash mark in the tables with Female 1 to the left of the slash mark.

TABLE 1

NAIL PLATE DISTAL THICKNESS-LEFT HAND

| Day | Thumb | Index | Digitus medius | Digitus anularis | Digitus minimus |
|---|---|---|---|---|---|
| 0 | 0.00/0.00 | 0.00/0.00 | 0.00/0.00 | 0.00/0.00 | 0.00/0.00 |
| 7 | 0.10/0.10 | 0.00/0.10 | 0.00/0.10 | 0.10/0.00 | 0.00/0.05 |
| 14 | 0.30/0.20 | 0.10/0.20 | 0.05/0.10 | 0.10/0.20 | 0.05/0.05 |
| 21 | 0.45/0.30 | 0.40/0.30 | 0.10/0.25 | 0.30/0.40 | * /0.10 |
| 28 | 0.60/0.30 | 0.45/0.50 | 0.25/0.35 | 0.50/0.80 | —/0.20 |
| 35 | 0.60/0.35 | 0.45/0.50 | 0.30/0.35 | 0.50/0.80 | 0.10/0.30 |

*Nail broke off horizontally at the quick-unavailable for measurement

TABLE 2

NAIL PLATE DISTAL THICKNESS-RIGHT HAND

| Day | Thumb | Index | Digitus medius | Digitus anularis | Digitus minimus |
|---|---|---|---|---|---|
| 0 | 0.00/0.00 | 0.00/0.00 | 0.00/0.00 | 0.00/0.00 | 0.00/0.00 |
| 7 | 0.10/0.10 | 0.16/0.05 | 0.07/0.05 | 0.00/0.10 | 0.06/0.05 |

TABLE 2-continued

NAIL PLATE DISTAL THICKNESS-RIGHT HAND

| Day | Thumb | Index | Digitus medius | Digitus anularis | Digitus minimus |
|---|---|---|---|---|---|
| 14 | 0.10/0.10 | 0.10/0.05 | 0.10/0.05 | 0.15/0.15 | 0.07/0.05 |
| 21 | 0.30/0.30 | 0.20/0.20 | 0.30/0.10 | 0.40/0.50 | 0.10/0.20 |
| 28 | 0.40/0.30 | 0.25/0.20 | 0.40/0.20 | 0.60/0.70 | 0.25/0.30 |
| 35 | 0.40/0.30 | 0.30/0.30 | 0.40/0.30 | 0.60/0.80 | 0.30/0.30 |

TABLE 3

LONGITUDINAL NAIL GROWTH-LEFT HAND

| Day | Thumb | Index | Digitus medius | Digitus anularis | Digitus minimus |
|---|---|---|---|---|---|
| 0 | 14.0/11.0 | 12..0/11.0 | 12.0/10.9 | 12.0/9.4 | 10.0/9.0 |
| 7 | 15.2/11.8 | 12.7/11.5 | 13.0/11.1 | 12.8/10.0 | 10.4/9.4 |
| 14 | 16.9/14.2 | 13.8/12.4 | 14.1/11.6 | 14.4/11.2 | 16.5/10.0 |
| 21 | 18.8/15.8 | 14.5/13.5 | 15.6/11.9 | 17.6/13.0 | *10.0/11.5 |
| 28 | 21.0/18.1 | 15.0/14.4 | 18.0/12.5 | 19.0/16.4 | 12.4/12.6 |
| 35 | 22.0/19.2 | 16.6/15.0 | 13*/13.2 | 20.0/20.0 | 13.0/14.0 |

*Nail broke

TABLE 4

LONGITUDINAL NAIL GROWTH-RIGHT HAND

| Day | Thumb | Index | Digitus medius | Digitus anularis | Digitus minimus |
|---|---|---|---|---|---|
| 0 | 15.0/9.1 | 12.0/10.2 | 12.0/10.1 | 12.0/9.0 | 10.0/8.1 |
| 7 | 15.1/9.5 | 12.4/10.5 | 13.0/10.8 | 12.8/9.3 | 10.5/8.4 |
| 14 | 16.5/11.0 | 13.0/11.0 | 15.4/11.4 | 14.0/10.0 | 11.4/9.0 |
| 21 | 18.2/13.4 | 14.2/11.8 | 16.4/12.2 | 17.0/11.1 | 12.2/10.1 |
| 28 | 22.0/15.2 | 16.5/12.8 | 17.1/13.0 | 18.6/12.4 | 13.0/12.2 |
| 35 | 23.0/18.0 | 17.0/14.0 | 17.5/14.0 | 18.8/14.4 | 14.2/14.0 |

Modifications and variations of the present compositions and methods for promoting keratinization will be obvious to those skilled in the art from the foregoing detailed description. Such modifications and variations are intended to come within the scope of the appended claims.

I claim:

1. A method for promoting keratinization resulting in hair or nail growth comprising administering to a human or animal an effective amount of a benzimidazole anthelmintic selected from the group consisting of thiabendazole, cambendazole, mebendazole, flubendazole, ciclobendazole, fenbendazole, oxfendazole, albendazole, and oxibendazole.

2. The method of claim 1 wherein the nail is infected with fungus and an effective amount of the benzimidazole is administered topically to the fungally infected nail.

3. The method of claim 1 wherein the benzimidazole is administered orally.

4. The method of claim 1 wherein the benzimidazole is administered topically.

5. The method of claim 1 wherein the benzimidazole is selected from the group consisting of fenbendazole and oxfendazole.

* * * * *